(12) United States Patent
Ganesan et al.

(10) Patent No.: US 7,863,209 B2
(45) Date of Patent: *Jan. 4, 2011

(54) METHODS FOR RECYCLING CATALYST COMPOSITIONS FOR AROMATIC RING HALOGENATION

(75) Inventors: Balakrishnan Ganesan, Maharashtra (IN); Pradeep Jeevaji Nadkarni, Karnataka (IN); Robert Edgar Colborn, Niskayuna, NY (US); Dan Hancu, Clifton Park, NY (US)

(73) Assignee: Sabic Innovative Plastics IP B.V. (NL)

( * ) Notice: Subject to any disclaimer, the term of this patent is extended or adjusted under 35 U.S.C. 154(b) by 1017 days.

This patent is subject to a terminal disclaimer.

(21) Appl. No.: 10/870,352

(22) Filed: Jun. 16, 2004

(65) Prior Publication Data
US 2005/0283034 A1 Dec. 22, 2005

(51) Int. Cl.
*B01J 38/42* (2006.01)
*B01J 38/50* (2006.01)
*B01J 31/00* (2006.01)
*C07C 25/00* (2006.01)
*C01G 3/04* (2006.01)
*C01G 5/00* (2006.01)
*C01G 7/00* (2006.01)
*C22B 3/00* (2006.01)
*C22B 11/06* (2006.01)
*C01G 49/10* (2006.01)

(52) U.S. Cl. .......................... 502/35; 502/29; 502/161; 502/168; 570/208; 570/209; 570/210; 423/46; 423/493

(58) Field of Classification Search .......... 570/182, 570/190, 207, 209, 210; 502/161, 168, 29, 502/35, 514; 423/46, 493
See application file for complete search history.

(56) References Cited

U.S. PATENT DOCUMENTS

| | | | |
|---|---|---|---|
| 3,226,447 A | 12/1965 | Bing et al. | |
| 3,622,640 A | 11/1971 | Taylor et al. | |
| 3,931,340 A * | 1/1976 | Nishihara et al. | 568/746 |
| 4,031,142 A | 6/1977 | Graham | |
| 4,031,145 A | 6/1977 | Di Bella | |
| 4,031,147 A | 6/1977 | Graham | |
| 4,190,609 A | 2/1980 | Lin | |
| 4,250,122 A | 2/1981 | Lin et al. | |
| 4,289,916 A | 9/1981 | Nakayama et al. | |
| 4,647,709 A | 3/1987 | Wolfram | |
| 4,827,058 A | 5/1989 | Mais et al. | |
| 4,925,994 A | 5/1990 | Mais et al. | |
| 5,210,343 A | 5/1993 | Mais et al. | |

FOREIGN PATENT DOCUMENTS

| | | |
|---|---|---|
| JP | 60125251 | 7/1985 |
| WO | WO 97/43041 | 11/1997 |
| WO | WO 2004/082826 | 9/2004 |

OTHER PUBLICATIONS

Kiji et al. JP 60-125251. "Catalyst for Halogenating Nucleus of Alkylbenzene." Patent Abstracts of Japan. Jul. 4, 1985. Abstract.*
J. Krishna Murthy et al. "Mixed Metal Fluorides as Doped Lewis Acidic Catalyst Systems: A Comparative Study Involving Novel High Surface Area Metal Fluorides", Journal of Fluorine Chemistry, vol. 125, pp. 937-949, 2004.

* cited by examiner

*Primary Examiner*—Steven Bos
*Assistant Examiner*—Anthony J Zimmer
(74) *Attorney, Agent, or Firm*—Cantor Colburn LLP

(57) ABSTRACT

A method for recovering and reusing a ring-halogenation catalyst comprises: (A) contacting an aromatic compound with chlorine or bromine in the presence of a catalyst composition, where the catalyst composition comprises at least one salt comprising a Group 4-13 metal, a lanthanide metal, or an actinide metal; and at least one organic counterion derived from an organic acid having a pKa relative to water of 0 or greater; and at least one organic sulfur compound; to form a first product mixture comprising a monochloro or a monobromo aromatic compound and a Group 4-13 metal halide, a lanthanide metal halide or an actinide metal halide; (B) separating the metal halide from the first product mixture; and (C) contacting at least a portion of the metal halide and an aromatic compound with chlorine or bromine, and at least one organic sulfur compound; to form a second product mixture comprising a monochloro or a monobromo aromatic compound and a Group 4-13 metal halide, a lanthanide metal halide or an actinide metal halide.ving a pKa relative to water of 0 or greater; and at least one organic sulfur compound.

16 Claims, No Drawings

METHODS FOR RECYCLING CATALYST COMPOSITIONS FOR AROMATIC RING HALOGENATION

BACKGROUND

This invention relates to methods for recovering and recycling a catalyst composition used for ring-halogenating aromatic compounds. More particularly, it relates to methods for recycling and using such catalyst compositions, which are capable of producing predominantly para-halo aromatic compounds.

Chlorination of aromatic compounds such as toluene and xylenes is a known reaction affording useful compounds. The most useful of these compounds for many purposes are the para-chloro aromatic compounds. para-Chlorotoluene, for example, is an intermediate capable of conversion into many useful chemicals. para-Chloro-ortho-xylene (also sometimes referred to as 4-chloro-1,2-dimethylbenzene) is another useful compound, which can be oxidized to 4-chlorophthalic acid, which is in turn an important intermediate in the production of polyetherimides. However, the production of these useful para-chloroaromatic compounds is complicated by the simultaneous production of numerous undesirable by-products. Thus, chlorination of toluene and xylenes (ortho-xylene and ortho-xylene) produces the para-monochloro isomer in admixture with other isomers, such as ortho-chlorotoluene and 3-chloro-1,2-dimethylbenzene, respectively. In addition, numerous polychlorinated products are also generally produced.

Many of the known methods for chlorination of aromatic compounds involve reaction with elemental chlorine in the presence of Lewis acids, such as for example, ferric chloride, antimony trichloride, antimony pentachloride, zinc chloride and aluminum chloride, which are also generally used as catalysts in Friedel-Crafts reactions, such as alkylation and acylation.

However, the use of such catalysts generally does not lead to enhanced selectivity for the desired para-chloroaromatic isomer and minimized formation of polychlorinated products. Various publications, including many U.S. patents, go further in describing mixed catalyst systems in which another catalyst component is an organosulfur compound. The organosulfur compounds disclosed in these publications are of very diverse structures. Some examples of organosulfur compounds that have been used include phenoxathiins, thianthrenes, and phenothiazines. Illustrative patents are U.S. Pat. Nos. 3,226,447, 4,031,142, 4,031,145, 4,031,147, 4,190,609, 4,250,122, 4,289,916, 4,647,709, 4,925,994, and 5,210,343; and European Patent Application No. 126669. Such conditions are far from ideal for commercial practice. Progress in the field of para halogenation of aromatic compounds notwithstanding, there remains a strong need to develop further improvements both in terms of product yield and selectivity.

BRIEF SUMMARY

The present invention describes methods for recovering, reusing, and recycling catalysts for ring-halogenating aromatic compounds with no significant loss in selectivity for forming para-chloro aromatic compounds.

In one embodiment of the present invention, a method for recovering and reusing a ring-halogenation catalyst comprises: (A) contacting an aromatic compound with chlorine or bromine in the presence of a catalyst composition, where the catalyst composition comprises at least one salt comprising a Group 4-13 metal, a lanthanide metal, or an actinide metal; and at least one organic counterion derived from an organic acid having a pKa relative to water of 0 or greater; and at least one organic sulfur compound; to form a first product mixture comprising a monochloro or a monobromo aromatic compound and a Group 4-13 metal halide, a lanthanide metal halide or an actinide metal halide; (B) separating the metal halide from the first product mixture; and (C) contacting at least a portion of the metal halide and an aromatic compound with chlorine or bromine, and at least one organic sulfur compound; to form a second product mixture comprising a monochloro or a monobromo aromatic compound and a Group 4-13 metal halide, a lanthanide metal halide or an actinide metal halide.

In a second embodiment of the present invention, a method for recovering and reusing a ring-halogenation catalyst comprises: (A) contacting an aromatic compound with chlorine in the presence of a catalyst composition, where the catalyst composition comprises at least one salt comprising a Group 4-13 metal, a lanthanide metal, or an actinide metal; and at least one organic counterion derived from an organic acid having a pKa relative to water of 0 or greater; and at least one organic sulfur compound; to form a first product mixture comprising a monochloro aromatic compound and a Group 4-13 metal chloride, a lanthanide metal chloride or an actinide metal chloride; (B) separating the metal chloride from the first product mixture; and (C) contacting at least a portion of the metal chloride and an aromatic compound with chlorine, and at least one organic sulfur compound; to form a second product mixture comprising a monochloro aromatic compound and a Group 4-13 metal chloride, a lanthanide metal chloride or an actinide metal chloride.

In a third embodiment of the present invention, a method for recovering and reusing a ring-chlorination catalyst comprises: (A) contacting ortho xylene with chlorine in the presence of copper salt of formula Cu(Y)X, where Y comprises an organic counterion derived from an organic acid, which has a pKa relative to water of 0 or greater; and X is Cl, Br, I, or $(SO_4)_{1/2}$, to form a first product mixture comprising a monochloro ortho xylene and copper(II) chloride; (B) separating said copper(II) chloride from the first product mixture; and (C) contacting at least a portion of the copper(II) chloride and ortho xylene with chlorine, and at least one organic sulfur compound; to form a second product mixture comprising a monochloro ortho xylene and copper(II) chloride.

DETAILED DESCRIPTION

The embodiments described above have many advantages, such as providing catalyst compositions, and methods for using and recycling these catalyst compositions to promote efficient para-selective ring-halogenations of aromatic compounds, such as toluene and ortho-xylene.

Any aromatic compound may be chlorinated by the methods disclosed herein. Suitable aromatic compounds include monocyclic and polycyclic hydrocarbons, and substituted derivatives thereof. Non-limiting examples of monocyclic hydrocarbons include benzene, toluene, ortho-, meta-, and para-xylene; and 1,2,4,5-tetramethylbenzene. It is preferred that the aromatic hydrocarbon contains at least one $C_{1-4}$ alkyl substituent, preferably methyl, and that a para-position with respect to one of the alkyl groups be substituted with hydrogen. Most preferred are toluene and o-xylene.

In an embodiment of the invention, the aromatic compound is contacted with chlorine in the presence of a catalyst composition to effect reaction. For liquid aromatic compounds, chlorine gas is generally bubbled through the liquid reactant. A solvent may be used with liquid aromatic compounds, although solvent is ordinarily not necessary. For aromatic compounds that are solids at ambient temperatures, a solvent can be beneficially used. Typically, the reaction takes place preferably in the liquid phase rather than in the vapor phase.

For the sake of brevity, the constituents of the catalyst composition are defined as "components" irrespective of whether a reaction involving said constituents occurs before or during the chlorination reaction. Thus, the catalyst composition may include the reaction products derived from one or more of the components. Such reaction products may comprise a chlorine atom source, such as chlorine, hydrogen chloride, or various combinations of chlorine and hydrogen chloride. Further, such reaction products may or may not be in admixture with one or more unreacted components remaining in the catalyst combination. Generally, the catalyst composition is obtained by combining components (A), (B), and (C).

Component A of the catalyst combination is at least one compound, most often a salt, of a metal selected from Groups 4-13, a lanthanide or an actinide of the Periodic Table of Elements. In some specific embodiments the metal is at least one member selected from the group consisting of copper, nickel, cobalt, manganese, molybdenum, zirconium, titanium, vanadium, niobium, palladium, indium, thallium, and platinum. Although it is not necessary for the metal salt to be soluble in the reaction medium, preferred salts include those that are at least partially soluble in the reaction medium. Included in this sub-category are salts where the anion (also hereinafter sometimes called the counterion) is derived from an acidic organic compound. Such salts have at least some solubility in a hydrophobic, organic solvent, such as for example, toluene and ortho-xylene. Illustrative examples of such acidic organic compounds include, but are not limited to, those with an approximate pKa value relative to water in a first embodiment of zero to about 1, in a second embodiment of at least about 1, in a third embodiment of at least about 2, in a fourth embodiment of at least about 3, in a fifth embodiment of at least about 4, in a sixth embodiment of at least about 5, in a seventh embodiment of at least about 6, and in an eighth embodiment of at least about 7, in a ninth embodiment of at least about 8, and in a tenth embodiment of at least about 9. In some embodiments, the anion is derived from a carboxylic acid, such as for example, a monocarboxylic acid, or a dicarboxylic acid; a 2,4-dione, or a derivative thereof. By "2,4-dione" is meant a 1,3-dicarbonyl compound, including, but not limited to, a diketone or a beta-ketoester in which a carbon atom separates the two carbonyl groups, irrespective of the placement of said carbonyl groups in the molecule. Illustrative examples of derivatives of carboxylic acids or 2,4-diones include halogenated derivatives and particularly chlorinated or fluorinated derivatives. Other non-limiting examples of counterions derived from organic acids include phosphate, phosphonate, alkoxide, phenoxide, and the like. Specific examples of salts suitable as component (A) include, but are not limited to cupric acetate, cupric 2,4-pentanedionate, cupric 1,1,1,5,5,5-hexafluoro-2,4-pentanedionate, cupric 1,1,1-trifluoro-2,4-pentanedionate, cupric benzoate, nickel acetate, nickel 2,4-pentanedionate, nickel 2,2,6,6-tetramethyl-3,5-heptanedionate, cobalt(II) acetate, cobalt(II) stearate, cobalt(II) 2,4-pentanedionate, manganese(II) acetate, manganese(II) stearate, manganese(II) 2,4-pentanedionate, thallium oxalate, indium oxalate, indium(III) trifluoroacetate, thallium(III) trifluoroacetate, molybdenum oxide bis(2,2,6,6-tetramethyl-3,5-heptanedionate), zirconium 2,4-pentanedionate, zirconium 1,1,1-trifluoro-2,4-pentanedionate, titanium oxide bis(2,4-pentanedionate), vanadium 2,4-pentanedionate, niobium 2,2,6,6-tetramethyl-3,5-heptanedionate, palladium 1,1,1,5,5,5-hexafluoro-2,4-pentanedionate, platinum 2,4-pentanedionate, cupric (benzoate)chloride, cupric (benzoate)bromide, cupric(benzoate)sulfate; cupric(acetate)chloride, cupric(acetate)bromide, cupric(acetate)sulfate, cupric(trifluoroacetate)chloride, cupric(trifluoroacetate)bromide, cupric (trifluoroacetate)iodide, cupric(trifluoroacetate)sulfate, cupric(stearate)chloride, cupric(stearate)bromide, and cupric (stearate)sulfate, cupric(pentafluorophenylbenzoate)chloride, cupric(pentafluorophenylbenzoate)bromide, and cupric (pentafluorophenylbenzoate)sulfate. Combinations of various salts can also be used. Cupric benzoate and cupric (benzoate)chloride are preferred since they are inexpensive and available commercially or easy to prepare. Component (B) is at least one organic sulfur compound. Suitable compounds include dialkyl and diaryl sulfides, dialkyl and diaryl disulfides, alkyl and aryl mercaptans, phenoxathiin, thiophene, dibenzothiophene, thianthrene and phenothiazine, including substituted derivatives thereof. Component B may also be a mixture of organic sulfur compounds.

A particularly preferred organic sulfur compound is phenothiazine-N-carbonyl chloride, having the formula

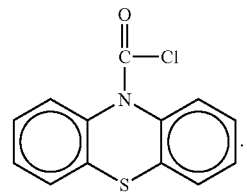

It may be synthesized by known methods such as the reaction of phenothiazine with phosgene. Also particularly effective is N-trifluoroacetylphenothiazine. Substituted analogs of N-trifluoroacetylphenothiazine, for example where the substituent is located on the aromatic ring, such as for example, 2-chloro-N-trifluoroacetylphenothiazine and 2-trifluoromethyl-N-trifluoroacetylphenothiazine are also effective.

Component (C) is a source of halide atoms such as a dihalogen, or a hydrogen halide, such as hydrogen chloride. In some circumstances, organic sulfur compounds, such as phenothiazine-N-carbonyl chloride can also act as a source of halide atoms, in addition to their role as a cocatalyst (Component B). In an embodiment, the hydrogen halide can be a commercially available material, such as for example hydrogen chloride gas from a cylinder. In another embodiment, the hydrogen halide is generated in-situ from the electrophilic aromatic substitution reaction of an aromatic compound with a source of electrophilc halogen. Without wishing to be bound by any theory, Applicants believe that component (C) reacts rapidly with the metal salt to generate a metal halide in a finely divided state, which in combination with the organic sulfur compound leads to selective halogenation of the aromatic compound.

The reaction of externally provided Component (C) with a metal salt is a valuable method for producing suspensions of finely divided metal halides, which can be used as catalysts having high activity, not only for aromatic halogenations, but also for any reaction which requires a Lewis acid catalyst, such as for example, the Friedel Crafts reaction and other related reactions. The process of generating the metal halide can be conducted in any organic solvent that is chemically inert to the hydrogen halide. Suitable organic solvents include saturated hydrocarbon solvents, such as for example, pentane, hexane, heptane, octane, decane, tetralin, and the like;

and aromatic hydrocarbons, such as for example, toluene, xylene, mesitylene, and the like.

The method of chlorinating aromatic compounds, as disclosed herein, takes advantage of the fact that either the chlorine directly, or the hydrogen halide generated in-situ from electrophilic aromatic substitution reaction of a source of electrophilic halogen with an aromatic compound reacts rapidly with the metal salt to generate the finely divided metal halide, which together with the organic sulfur compound leads to formation of selectively halogenated aromatic compounds. The method of the invention may be performed by contacting a mixture of the aromatic compound, component (A), and component (B) with chlorine, preferably in the liquid phase, most often at a temperature in the range of about 0-100° C., preferably about 5-50° C., and most preferably below 25° C. Preferably, the reaction mixture is protected from air and moisture by contact with an inert gas such as nitrogen or argon, and is shielded from exposure to ambient light to minimize chlorination of alkyl side chains on the aromatic compound. The term "light" in this context means radiation in the visible and ultraviolet regions of the spectrum. It is also important to shield the reaction mixture from moisture. The level of moisture in the aromatic compound to be halogenated should be preferably less than or equal to about 50 parts per million in one embodiment, more preferably less than or equal to about 25 parts per million in another embodiment.

On a preparative scale, contact is preferably accomplished by passing at least a portion, and more preferably substantially all of the chlorine through the reaction mixture. However, for screening purposes, it is often convenient to charge the chlorine to the head space of the reaction system, and to remove by-product hydrogen chloride by applying a slight vacuum. The pressure at which the reaction is carried out may vary from sub-atmospheric to super-atmospheric, for example from about 0.5-10 atmospheres, although super-atmospheric pressure is generally not necessary. It is also within the scope of the invention to generate chlorine in situ from a reagent such as thionyl chloride, sulfuryl chloride, phosgene, oxalyl chloride, N-chlorosuccinimide, and the like. On a preparative scale, chlorine gas can simply be passed into the mixture with periodic sampling until the desired or maximum amount of the desired para-monochloroaromatic compound product has been produced, as determined by analytical methods known in the art; for example, gas chromatography. For screening purposes it has been found convenient to employ an excess of chlorine, typically up to about 50 mole %, and preferably about 10-30 mole % relative to the aromatic compound. On a preparative scale, however, the use of excess chlorine is undesirable. In preparative scale reactions, excess chlorine is generally to be avoided due to over-chlorination. Typically, 25-100 mole percent, preferably 50-90 mole percent, and most preferably 70-85 mole percent of chlorine is employed relative to the amount of aromatic compound being chlorinated. In the preparative reactions, the efficiency for use of the chlorine is nearly 100 percent, so excess chlorine inevitably leads to over-chlorination.

The proportion of component (A) is typically in a range of from about 0.005 to about 10.0%, and the proportion of component (B) is in a range of from about 0.005 to about 10.0% by weight based on the weight of the aromatic compound. Preferably, the proportions of components (A) and (B) are, respectively, about 0.01-5.0% and about 0.01-0.1%, and most preferably about 0.07-3.0% and about 0.05-0.1%. The weight ratio of component (A) to component (B) is in various embodiments in a range of between about 2000:1 and 1:2000. The weight ratio of component (A) to component (B) is in some particular embodiments in a range of between about 2:1 and about 100:1; in other embodiments in a range of between about 3:1 and about 80:1; and in still other embodiments in a range of between about 3:1 and about 70:1.

The invention can be illustrated by taking copper(II) benzoate as a metal salt for chlorinating ortho-xylene. When chlorine is bubbled through a solution of ortho-xylene containing copper(II) benzoate and PNCC, a finely divided suspension is obtained at a very early stage of the chlorination reaction. Applicants have found that this copper(II) chloride shows a surprisingly higher catalytic activity and high selectivity, as compared with chemically identical, but commercially available samples of copper(II) chloride. Without wishing to be bound by any theory, Applicants believe that the formation of copper(II) chloride occurs by a rapid reaction of copper(II) benzoate with a chloride atom source, such as hydrogen chloride generated from reaction of ortho-xylene with electrophilic chlorine; and it is this copper(II) chloride that functions as a very active and regioselective catalyst for forming monochloro ortho-xylenes and 4-chloro-ortho-xylene with high selectivities. Further, Applicants have found that the copper(II) chloride generated in-situ can be recycled for a second and a third chlorination reaction without any significant loss in catalytic activity and selectivity for monochloro ortho-xylenes and 4-chloro-ortho-xylene. Furthermore, the in-situ generated metal halide in combination with an organic sulfur compound shows a surprisingly higher catalytic activity and selectivity for forming the para-chloroaromatic compound. Empirical observations indicate that a metal salt that is relatively more soluble in the hydrophobic solvent leads to a metal chloride having a relatively smaller particle size. Metal salts having fluorine-containing 2,4-pentanedione groups are generally more soluble in a hydrophobic solvent, and hence would be expected to generate relatively smaller particles of the metal halide.

Under the reaction conditions employed for halogenation of aromatic compounds, the reaction of hydrogen halide with a metal salt can proceed to generate one or more metal halide catalyst species. For example, if zirconium tetrakis(acetylacetonate) is used as the metal salt, various metal chloride catalyst species corresponding to the formula, $Zr(AcAc)_m Cl_{4-m}$, where "m" has a value of 1 to 3, are generated initially. However, as the chlorination of the aromatic compound continues, these initially formed catalyst species eventually transform into highly active, finely divided zirconium(IV) chloride, which together with the organic sulfur compound promotes the selective para-halogenation of the aromatic compound.

The reactive metal halides prepared as described above can also serve as valuable materials for other chemical transformations, such as for example Friedel-Crafts reactions, aldol reactions, and organometallic reactions, such as for example, preparation of organocopper compounds.

In an alternative method for chlorinating an aromatic compound, a two-step process can be used in which the first step is the reaction of the metal salt with hydrogen chloride gas in any solvent that is inert to hydrogen chloride, and to the combination of a metal chloride and hydrogen chloride. Examples of such inert solvents include saturated linear hydrocarbons, aromatic hydrocarbons, and saturated cyclic hydrocarbons. Some non-limiting examples of solvents include hexane, heptane, octane, toluene, xylene, decalin, and the like. After forming the finely divided metal chloride, as described above, the metal chloride can be isolated and combined with an organic sulfur compound and used as an active catalyst composition for ring-chlorinating an aromatic compound with high selectivity for monochloro ortho-xylenes and 4-chloro-ortho-xylene. In a preferred embodiment, the first step is carried out in an aromatic hydrocarbon solvent, such as ortho-xylene, which also serves as the substrate for the subsequent ring chlorination step.

While the present invention is not dependent in any way on theory or reaction mechanism, it is believed that these differences in proportion of metal compound are the result of different reaction mechanisms. With a relatively strong Lewis acid such as ferric chloride as Component (A), it is believed that complex formation with component (B) minimizes the level of non-selective aromatic ring chlorination catalyzed by the Lewis acid alone, and promotes selective chlorination with production of the para-monochlorinated isomer. The copper-based Lewis acids employed according to the present invention, by contrast, are relatively weak and their presence in relatively large proportions is not as likely to afford non-selective aromatic chlorination, although selectivity is improved by the presence of component (B). When aromatic compounds having alkyl substituents are used, at low Lewis acid levels, side chain chlorination predominates to yield products that are undesirable for the purposes of the present invention.

Copper(II) salts of formula Cu(Y)X, where Y comprises a counterion derived from an organic acid having a pKa relative to water of 0 or greater; and X comprises Cl, Br, I, or $SO_4$, are also suitable examples of metal salts which can be used in aromatic ring halogenations. These salts are prepared by contacting inorganic copper(II) salts, such as copper(II)chloride, copper(II) bromide, copper(II) iodide, copper(II)sulfate, or mixtures thereof, with an stoichiometric quantity of a salt of an organic acid, preferably an alkali metal salt of an organic acid having a pKa relative to water of 0 or greater. Preferred organic acid metal salts are lithium, sodium, potassium, rubidium, or cesium salts of monocarboxylic acids and dicarboxylic acids. Any solvent in which the inorganic copper(II) salt is soluble can be used. Preferred solvents are those in which the starting inorganic copper(II) salt is soluble, but in which solvent the Cu(Y)X salts are insoluble, to allow for easy isolation of the product. Preferred solvents are those comprising water or $C_1$-$C_4$ aliphatic alcohols.

In situations where conditions are optimized for production of the desired para-chloroaromatic compound, it may be possible to employ the chlorination product of the method of the invention directly for further purposes, for example as a chemical intermediate, without further purification. Sometimes, however, further purification is desirable or necessary. Purification may be achieved by the use of one or more conventional purification techniques, including fractional distillation, fractional crystallization, and preparative-scale chromatographic methods.

The catalyst composition comprising the copper salts (Component A) and the organic sulfur compound can also be recovered from the chlorination reaction mixture for repeated use in subsequent reactions. Care must be taken to exclude moisture during the recovery and recycle of the catalyst back to the chlorination reactor. In one embodiment, catalyst recovery may be achieved by removing, at least in part, other components of the product mixture, typically by distillation or evaporation, and filtering. In another embodiment, the reaction mixture is allowed to stand until the catalyst composition settles at the bottom of the reactor. Settling of the catalyst composition can also be accelerated using techniques such as centrifugation. The supernatant clear organic liquid is separated by techniques known in the art, such as decantation, trituration, suction through a dip tube, filtration using a filter made of a non-corrosive material, such as Teflon, and the like. The filtrate may then be evaporated to remove, either partially or fully, the volatile organic components and furnish the metal halide. When this metal halide, or at least a portion of this metal halide is combined with component (B) as previously described, and employed for a second chlorination run, the reaction proceeds just as in the first run. Using any of the described techniques, the catalyst composition can be recovered and recycled at least three times without any significant loss in catalytic activity and selectivity for the para-chloroaromatic compound. The halogenation methods described hereinabove can be carried out in a batch, a semi-batch, or a continuous process.

The catalyst compositions taught herein may be employed for any reaction catalyzed by (1) the combination of (A) at least one Group 4-13 metal, and (B) at least one organic sulfur compound; (2) a reaction product comprising (A) and (B), (3) the components (A), (B), and a reaction product comprising at least one of (A) or (B), or (4) (B) and a reaction product of component (A) with a halogen atom source, such as hydrogen halide (as described previously).

The catalyst compositions and methods disclosed herein are especially useful for producing 4-chloro-ortho-xylene by the chlorination of ortho-xylene, and allow high ortho-xylene conversion while keeping the selectivity for mono-chloro-ortho-xylene at relatively high levels, and formation of over-chlorinated products at relatively lower levels. This increases the efficiency of recovering purified 4-chloro-ortho-xylene by downstream operations, such as distillation, and also decreases the cost of recovery and recycle of unreacted ortho-xylene by distillation.

EXAMPLES

The invention is illustrated by the following examples. All percentages are by weight. Example numbers with an asterisk ("*") after the number indicate comparative examples. The abbreviation "PNCC" stands for phenothiazine-N-chlorocarbonyl chloride. "Conversion" is the percentage of ortho-xylene converted to chlorinated products. The abbreviation "mono-Cl" designates the amount of aromatically monochlorinated ortho-xylene products (i.e., products in which the aromatic ring is monochlorinated as opposed to those in which the side chain is chlorinated) as a percentage of total chlorinated products, and "4-Cl" designates the amount of the 4-monochloro (p-chloro) ortho-xylene isomer as a percentage of total aromatically monochlorinated products. While the experimental examples provided herein are limited to the recovery and recycle of copper (II) chloride, the method of the present invention may be applied to effect the recovery, recyle and reuse of any Group 4-13 metal chlorination catalyst in any halogenation reaction.

Example 1

This Example describes the preparative scale chlorination of ortho-xylene using copper benzoate as Component (A) and PNCC as the organic sulfur compound (Component B).

In a 2-liter, four necked round bottom flask fitted with an overhead stirrer, a gas bubbler for chlorine gas, a gas outlet connected in series with a scrubber containing 1,2-dichlorobenzene (to trap any vapors of organic material coming from the chlorination reactor, and prevent ingress of moisture from the water trap to the chlorination reactor), water and alkali scrubbers; and a thermometer, was placed ortho-xylene (1100 grams), PNCC (0.22 gram), and copper benzoate (8.8 grams, pre-dried at 50° C. for 48 hours). The reaction flask was covered to avoid exposure of the reaction mixture to ambient light during the chlorination reaction. The contents of the flask were cooled while stirring to about 5° C., and chlorine gas was introduced at the rate of 1.5-2 moles per hour. The reaction was exothermic, and the reaction temperature was maintained at a between about 5-8° C. by externally cooling the reaction mixture, as well as by controlling the flow of chlorine. Within the first two minutes of passing chlorine gas, a brown precipitate was formed, which was sampled and confirmed by powder X-ray diffraction and inductively coupled plasma analyses to be copper(II) chloride. The passage of chlorine gas was continued, and the reaction was monitored for ortho-xylene conversion by gas chromatography. When an ortho-xylene conversion of 70-75% was reached, the chlorine flow into the reaction mixture was stopped, and thereafter nitrogen was bubbled through the reaction mixture for about 30 minutes to remove unreacted chlorine gas as well as dissolved hydrogen chloride gas.

The same procedure was repeated with a commercial sample of copper(II) chloride (Comparative Example 1), cupric acetate (Example 2), and cupric bis(1,1,1-trifluoroacetylacetonate) (Example 3). The results are shown in Table 1.

TABLE 1

| Example | Lewis acid Identity | wt %[a] | Conversion, % | Mono-Cl, % | 4-Cl, % |
|---|---|---|---|---|---|
| 1 | Cupric benzoate | 0.8 | 78 | 97 | 80 |
| 1* | CuCl$_2$ | 0.8 | 63 | 44 | 58 |
| 2 | Cupric acetate | 0.8 | 66 | 65 | 76 |
| 3 | Cupric bis(trifluoroacetylacetonate) | 0.44 | 87 | 98 | 82 |

[a]"wt %" refers to the amount of metal salt employed expressed as a percentage of the weight of o-xylene The data in Table 1 demonstrate clearly that cupric benzoate, cupric bis(trifluoroacetylacetonate) and cupric acetate function as effective metal halide salts in the monochlorination of aromatic compounds such as ortho-xylene. The experimental data (See Example 1) moreover show that these metal salts which act as precursors of the active copper(II) chloride, together with PNCC function as an effective catalyst composition for ortho-xylene chlorination. Further, the conversion and 4-chloro-ortho-xylene selectivity are much higher than with commercially available copper(II) chloride.

Example 4

This Example illustrates the recyclability of the copper(II) chloride catalyst generated in-situ from copper(II) benzoate used in the first chlorination run. The first ortho-xylene chlorination run was run as described in Example 1. The recovered catalyst, which is the active, finely divided form of copper (II) chloride was recycled for a second and third consecutive chlorination run as follows.

After sparging nitrogen gas through the reaction mixture to remove excess chlorine and hydrogen chloride, the reaction mixture was allowed to stand overnight under nitrogen atmosphere when the cupric chloride catalyst settled at the bottom of the reactor. Then about 90 weight percent of the supernatant reaction mixture was decanted under nitrogen atmosphere leaving a slurry of the brown cupric chloride in the reactor. To the slurry was added ortho-xylene and PNCC in the same quantities as used for the first chlorination run. No fresh addition of copper(II) benzoate was made. The second chlorination run was carried out as described above, and the chlorination reaction mixture was decanted away from the cupric chloride catalyst residue. The procedure was repeated for a third time as described hereinabove. The results are shown in Table 2.

Example 4

The procedure described in Example 3 was carried out using cupric bis(trifluoroacetylacetonate) (4.4 grams) as the salt, which leads to the formation of the active form of copper (II) chloride during the first ortho-xylene chlorination run. The active copper(II) chloride was used for a second consecutive chlorination run. Results are shown in Table 2.

TABLE 2

| Metal Salt | Run number | 4-Cl (%) |
|---|---|---|
| Copper (II) benzoate | 1 | 82 |
|  | 2 | 82 |
|  | 3 | 82 |
| Cupric bis(trifluoroacetylacetonate) | 1 | 82 |
|  | 2 | 82 |

The results in Table 2 show that the copper(II) chloride catalyst generated in-situ from cupric benzoate or cupric bis (trifluoroacetylacetonate) can be recycled and re-used without any appreciable decrease in 4-chloro-ortho-xylene selectivity.

Example 5

This Example describes the preparation of copper(benzoate) chloride.

Equimolar quantities of copper(II) chloride and sodium benzoate were separately weighed out and dissolved in water. The sodium benzoate solution was added to the solution of copper(II) chloride with stirring. The resulting precipitate of copper(benzoate)chloride was filtered, washed with water until the washings did not contain any sodium benzoate or copper (II) chloride, then washed with acetone to remove any unreacted sodium benzoate, and finally dried to furnish the desired product as a pale blue solid.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:
1. A method for recovering and reusing a ring-halogenation catalyst, said method comprising:
(A) contacting an aromatic compound with chlorine or bromine in the presence of a catalyst composition, said catalyst composition comprising at least one salt comprising copper and at least one organic counterion derived from an organic acid having a pKa relative to water of 0 or greater and selected from the group consisting of a dicarboxylic acid, a 2,4-dione, and derivatives of the foregoing acids; and at least one organic sulfur compound; to form a first product mixture comprising copper chloride and a monochloro aromatic compound;
(B) separating copper chloride from said first product mixture, and
(C) contacting at least a portion of the separated copper chloride and an aromatic compound with chlorine, and at least one organic sulfur compound; to form a second product mixture comprising copper chloride and a monochloro aromatic compound.

2. The method of claim 1, wherein said separating comprises at least one step selected from the group consisting of a decantation step, a filtration step, a trituration step, a centrifugation step, and an evaporation step.

3. The method of claim 2, wherein said separating comprises a decantation step.

4. The method of claim 1, further comprising:
(D) separating copper chloride from said second product mixture, thereby forming a second separated copper chloride.

5. The method of claim 4, further comprising:
(E) contacting at least a portion of said second separated copper chloride separated in step (D) with an aromatic compound with chlorine, and at least one organic sulfur compound; to form a third product mixture comprising a monochloro aromatic compound.

6. The method of claim 1, wherein said contacting in step (A) comprises a reaction temperature of about 0-100° C.

7. The method of claim 1, wherein said contacting in step (A) comprises shielding from exposure to ambient light and ambient moisture.

8. The method of claim 1, wherein the aromatic compound is a monocyclic hydrocarbon.

9. The method of claim 5, wherein the aromatic compound is toluene or ortho-xylene.

10. The method of claim 1, wherein said at least one salt of step (A) is selected from the group consisting of cupric 2,4-pentanedionate, cupric 1,1,1,5,5,5-hexafluoro-2,4-pentanedionate, cupric 1,1,1-trifluoro-2,4-pentanedionate, cupric benzoate, cupric (benzoate)chloride, cupric (benzoate)bromide, cupric(benzoate)sulfate; cupric(stearate)chloride, cupric(stearate)bromide, and cupric(stearate)sulfate, cupric(pentafluorophenylbenzoate)chloride, cupric (pentafluorophenylbenzoate)bromide, cupric bis (trifluoroacetylacetonate) and cupric (pentafluorophenylbenzoate)sulfate.

11. The method of claim 1, wherein said at least one organic sulfur compound is selected from the group consisting of a dialkyl or diaryl sulfide, a dialkyl or diaryl disulfide, an alkyl or aryl mercaptan, a phenoxathiin, a thiophene dibenzothiophene, a thianthrene or a phenothiazine.

12. The method of claim 1, wherein said at least one organic sulfur compound is selected from the group consisting of phenothiazine-N-carbonyl-1 chloride, N-trifluoroacetylphenothiazine, 2-chloro-N-trifluoroacetylphenothiazine or 2-trifluoromethyl-N-trifluoro acetylphenothiazine.

13. The method of claim 1, wherein said at least one salt of step (A) is present in an amount corresponding to about 0.005-10.0% by weight based on the aromatic compound.

14. The method of claim 1, wherein said at least one salt of step (A) is present in an amount corresponding to about 0.07-3.0% by weight based on the aromatic compound.

15. The method of claim 1, wherein said at least one organic sulfur compound is present in an amount corresponding to about 0.005-10.0% by weight based on the aromatic compound.

16. The method of claim 1, wherein said at least one organic sulfur compound is present in an amount corresponding to about 0.01-0.1% by weight based on the aromatic compound.

* * * * *